United States Patent [19]

Fuwa et al.

[11] Patent Number: 5,382,567

[45] Date of Patent: Jan. 17, 1995

[54] AROMATIC COMPOSITION AND METHOD FOR CONTROLLING AROMA

[75] Inventors: Toru Fuwa, Takata; Kaneto Uekama, Kumamoto, both of Japan

[73] Assignee: Wakunaga Seiyaku Kabushiki Kaisha, Osaka, Japan

[21] Appl. No.: 53,187

[22] Filed: Apr. 27, 1993

Related U.S. Application Data

[62] Division of Ser. No. 833,452, Feb. 6, 1992, Pat. No. 5,238,915.

[30] Foreign Application Priority Data

Feb. 8, 1991 [JP] Japan .................. 3-39325
Feb. 8, 1991 [JP] Japan .................. 3-39326

[51] Int. Cl.⁶ .................................................. A61K 1/46
[52] U.S. Cl. .................................................. 512/4
[58] Field of Search .................................................. 512/4

[56] References Cited

U.S. PATENT DOCUMENTS

| | | | |
|---|---|---|---|
| 4,582,635 | 4/1986 | Furuuchi et al. | 512/4 |
| 4,610,927 | 9/1986 | Igarashi et al. | 512/4 |
| 4,664,847 | 5/1987 | Williams | 512/4 |
| 4,708,973 | 11/1987 | Dohr | 512/4 |
| 4,842,761 | 6/1987 | Rutherford | 512/4 |
| 4,904,639 | 2/1990 | Hallam | 512/4 |
| 4,997,599 | 3/1991 | Steiner et al. | 512/4 |
| 5,188,753 | 2/1993 | Schmidt et al. | 512/4 |

FOREIGN PATENT DOCUMENTS

| | | | |
|---|---|---|---|
| 1124180 | 5/1981 | Canada | 512/4 |
| 50-63126 | 5/1975 | Japan | 512/4 |
| 55-78965 | 6/1980 | Japan | 512/4 |
| 63-254197 | 10/1988 | Japan | 512/4 |
| 1-274766 | 11/1989 | Japan | 512/4 |

*Primary Examiner*—James H. Reamer
*Attorney, Agent, or Firm*—Sughrue, Mion, Zinn, Macpeak & Seas

[57] ABSTRACT

Aromatic compositions which comprise perfumes included in cyclodextrins whose inclusion ability depends on a pH of a solution containing the perfumes and cyclodextrins and pH-adjusting substances whereby a release rate of the perfume can be controlled, are described. Aromatic compositions are also disclosed, which comprise perfumes coated or covered with materials whose solubility depends on the pH of a solution containing the coated perfumes, and a pH-adjusting substance to change the pH as desired. Methods for controlling the release rate of the perfumes are also described.

17 Claims, 4 Drawing Sheets

FIG. 5 ial perfumes which originate from natural plants and animals and whose aromatic ingredients are collected therefrom by physical and chemical treatments such as steam distillation, extraction and the like, chemical substances derived from resources such as coal, petroleum, natural gas, oils and fats, and perfumes prepared through chemical reactions of the natural perfumes and isolated perfumes, such as of oxidation, reduction, condensation, hydrolysis, substitution, addition and transition.

AROMATIC COMPOSITION AND METHOD FOR CONTROLLING AROMA

This is a divisional of application Ser. No. 07/833,452 filed Feb. 6, 1992 now U.S. Pat. No. 5,238,915.

BACKGROUND OF THE INVENTION

1. Field of the Invention

This invention relates to an aromatic composition which is effectively utilizable such as in aromatherapy and also to a control method of aroma.

2. Description of the Prior Art

In the overpopulated and complicated, present-day community, attention has been recently drawn to adverse influences of stress on human body. Under these circumstances, various studies have been made, including investigations on amenities with which life space is made comfortable, developments of related substances, and countermeasures against offensive odor and public nuisance. Especially, aroma greatly influences human physiology and psychology. Aromatherapy which makes use of the effects of herbs, populi and phytoncides has been extensively made in various fields including psychologic medicines such as on stress as well as aromatic science and chemistry.

Aromatic products which are utilizable in the aromatherapy have now been under extensive development. However, the emanation of aroma is difficult to control, thus presenting the problem on a fine or minute control of the aroma emanation.

SUMMARY OF THE INVENTION

It is accordingly an object of the invention to provide an aromatic composition which comprises a release-controlled perfume so that a release of the aroma or fragrance is minutely controllable.

It is another object of the invention to provide a control method of aroma wherein a release rate of a perfume is so controlled that the aroma or fragrance can be minutely controlled.

In order to attain the above objects, we made intensive studies and, as a result, found that when a perfume is included in a cyclodextrin whose inclusion ability in the form of a solution is changed depending on the pH. When the pH of the solution is changed, the perfume-including ability of the cyclodextrin is changed thereby easily controlling a release rate of an aroma to ensure a minute release control of the aroma. In addition, when a pH-adjusting substance is gradually added to the perfume-including cyclodextrin solution to gradually change the pH of the solution, the release of the perfume can be controlled as time passes. Moreover, when there are used a plurality of perfumes which have different aroma releasabilities at a given pH level, it becomes possible to cause different aromas to be released in relation to time. Such an aroma control method can be effectively utilized such as in aromatherapy.

According to one aspect of the invention, there is provided an aromatic composition which comprises at least one perfume, a cyclodextrin whose inclusion ability in a solution is changed depending on the pH of the solution, and a pH-adjusting substance.

According to another aspect, there is also provided a method for controlling an aroma which comprises including at least one perfume in a cyclodextrin whose inclusion ability is changed depending on the pH of a solution containing the at least one perfume and the cyclodextrin, and changing a pH of the solution by addition of a pH-adjusting substance to control a release rate of an aroma from the perfume.

Moreover, we found that when a perfume is coated or covered with a material whose solubility is changed depending on the pH of a solution and the pH of the solution is changed, the solubility of the coating material is changed whereby a degree of the release of the perfume can be readily controlled to ensure minute release control of the aroma from the perfume. In this case, when the types and amounts of perfume and coating material and the rate of addition of the pH substance are changed, a degree of the release of aroma may be arbitrarily varied, or different aromas may be released in relation to the variation in time. Such an aroma control method can be effectively utilized such as in aromatherapy.

Therefore, according to a further aspect of the invention, there is also provided an aromatic composition which comprises at least one perfume coated with a material whose solubility in a solvent is changed depending on the pH of a solution containing the coated at east one perfume, and a pH-adjusting substance.

According to a still further aspect of the invention, there is provided a method for controlling a release of at least one perfume which comprises providing at least one perfume coated with a material whose solubility in a solvent is changed depending on the pH, and changing the pH of a solution containing the coated at least one perfume by addition of a pH-adjusting substance to control a release rate of an aroma from the perfume.

DETAILED DESCRIPTION OF THE INVENTION

The perfumes used in the aromatic composition of the invention may be ones which is able to emanate aroma or fragrance. Examples of such perfumes include natu- Specific examples of the perfumes include animal perfumes such as musk oil, civet, castreum, ambergris, plant perfumes such as sandalwood oil, neroli oil, bergamot oil, lemon oil, lavender oil, sage oil, rosemary oil, peppermint oil, eucalyptus oil, verbena oil, citronella oil, cajuout oil, salvia oil, clove oil, chamomille oil, sandalwood oil, costus oil, labdanum oil, broom extract, carrot seed extract, jasmine extract, mimosa extract, narcissus extract, olibanum extract, rose extract and the like, and chemical substances such as acetophenone, dimethylindane derivatives, naphthalene derivatives, allyl caprate, α-amylcinnamic aldehyde, anethole, anisaldehyde, benzyl acetate, benzyl alcohol, benzyl propionate, borneol, cinnamyl acetate, cinnamyl alcohol, citral citronellal, cumin aldehyde, cyclamen aldehyde, decanol, ethyl butyrate, ethyl caprate, ethyl cinnamate, ethyl vanillin, eugenol, geraniol, hexenol, α-hexylcinnamic aldehyde, hydroxycitrolnellal, indole, iso-amyl acetate, iso-amyl iso-valerate, iso-eugenol, linalol, linalyl acetate, p-methylacetophenone, methyl anthranilate, methyl dihydrojasmonate, methyl eugenol, methyl-β-naphthol ketone, methylphenylcarbinyl acetate, musk ketol, musk xylol, 2,6-nanodinol, γ-nanolactone, phenylacetoaldehydodimethyl acetate, β-phenylethyl alcohol, 3,3,5-trimethylcyclohexanol, γ-undecalactone, undecenal, vanillin and the like. These perfumes may be used singly or in combination of two or more.

The amount of the perfume is generally the range of from 0.01 to 50 wt %, preferably from 0.1 to 30 wt %, based on the total of the aromatic composition, In the practice of the invention, the perfume may be included in cyclodextrins whose inclusion ability in a solution is changed depending on the pH of the solution, or may be coated with a material whose solubility in a solution is changed depending on the pH of the solution.

The cyclodextrins should be ones whose inclusion ability varies depending on a pH of a solution in which the cyclodextrins are placed. Such cyclodextrins are a series of compounds wherein when the pH of a cyclodextrin-containing solution is changed to either acidic or alkaline condition, the inclusion ability increased or decreased by a change in the between the molecular type and the ionic type which differ from each other in the behavior interaction with perfumes.

The cyclodextrins include, for example, sulfuric acid-substituted, amino-substituted, aminoalkyl-substituted, aminoalkyl and alkyl-substituted, carboxyalkyl-substituted, carboxyalkyl and alkyl-substituted, and phosphate-substituted derivatives of α, β or γ-cyclodextrin. Specific examples include carboxymethylethyl-β-cyclodextrin, carboxymethyl-β-cyclodextrin, diethylaminoethyl-βcyclodextrin, diethylamino-β-cyclodextrin, and the like.

The amount of the cyclodextrin is in the range of from 0.01 to 50 wt %, preferably from 0.1 to 5 wt %, based on the total aromatic composition. If the amount is less than 0.001 wt %, slow release of fragrance may, in some case, be unlikely to take place. Over 50 wt %, fragrance may be unlikely to be released.

On the other hand, the materials used to cover or coat the perfume should be ones whose solubility in a solution is changed depending on the pH Of the solution. For instance, those materials are usable wherein they are not or difficultly dissolved in a neutral condition or in the vicinity of the neutral condition but are dissolved in either acidic or alkaline condition. Examples of such coating materials include enteric coating materials, which are soluble in an alkaline condition, such as aminoalkylmethacrylate copolymers, methacrylic acid copolymers, hydroxypropylmethyl cellulose phthalate, hydroxypropylmethyl cellulose acetate succinate, carboxymethylethyl cellulose, cellulose acetate phthalate and the like, and gastric coating materials, which are soluble in an acidic condition, such as polyvinylacetal diethylaminoacetate and the like. The coating of the perfume with these materials may be performed by ordinary techniques.

The amount of the coating material is in the range of from 0.5 to 30 wt %, preferably from 3 to 15 wt %, based on the total aromatic composition. If the amount is less than 0.5 wt %, the coating film is not formed in a satisfactory thickness and may be immediately broken down when placed such as in water. Over 30 wt %, release of fragrance may be considerably delayed.

By changing the amount of the coating material, the release of aroma can easily be adjusted.

The aromatic composition of the invention should comprise a pH-adjusting substance in order to cause the perfume-including ability of the cyclodextrin or the solubility of the coating material to be properly controlled.

The pH-adjusting substances may any acidity or alkalinity-adjusting substances or mixtures thereof. Examples of the acidity-adjusting substances include mineral acids such as hydrochloric acid, sulfuric acid, boric acid, silicic acid and the like, organic carboxylic acids such as formic acid, citric acid, trichloroacetic acid, trifluoroacetic acid, benzoic acid, fumaric acid, tartaric acid and the like, and sulfonic acids such as methanesulfonic acid, benzenesulfonic acid, p-toluenesulfonic acid, mesitylenesulfonic acid, naphthalenesulfonic acid and the like. Examples of the alkaline adjusting substances include salts of alkali metals such as sodium, potassium and the like, salts of alkaline earth metals such as calcium, magnesium and the like, and ammonium salts, e.g. sodium chloride, sodium hydrogencarbonate, sodium carbonate, borax, sodium sulfate, potassium sulfide, sodium sulfide, sodium sesquicarbonate, potassium oxide, potassium nitrate, sodium nitrate, sodium polyphosphate, calcium carbonate, calcium hydrogenphosphate, potassium bromide, calcium chloride, ammonium chloride, iron sulfate, heavy magnesium carbonate, sodium phosphate, sodium thiosulfate and the like, and nitrogen-containing organic compounds such as trimethylamine, triethylamine, tributylamine, pyridine, N,N-dimethylaniline, N-methylpiperidine, N-methylmorpholine, diethylamine, cyclohexylamine, procaine, dibenzylamine, N-benzyl-β-phenetylamine, 1-ephenamine, N,N'-dibenzylethylenediamine and the like. When the carbonates are used as an alkaline adjusting substance in combination with organic acids, the aromatic composition may be prepared as effervescent.

The amount of the pH-adjusting substance may vary depending on the release rate of fragrance and the release time. In general, the amount is in the range from 50 to 1,000 parts by weight, preferably from 100 to 500 parts by weight, per 100 parts by weight of the cyclodextrin or coating material. It is preferred that when used, the aromatic solution containing the above ingredients can be adjusted to a pH range of from 3 to 9, preferably from 4 to 8.

The aromatic composition of the invention may further comprise arbitrary ingredients other than the above-stated essential ingredients, in amounts not impeding the effect of the aromatic composition. Such arbitrary ingredients include, for example, saccharides, surface active agents, oils and fats, high molecular weight compounds and the like. If a solvent is used, water or lower alcohols such as ethanol are preferably used.

The respective ingredients of the aromatic composition of the invention may be prepared and preserved in various forms prior to use provided that these ingredients can be mixed in a liquid medium on use.

For instance, a perfume, a cyclodextrin and a pH-adjusting agent may all be mixed to obtain a single mixture in the form of a solid or solution. Alternatively, the perfume and the cyclodextrin, and the pH-adjusting substance may be separated into two forms each as a solid or solution provided that the two forms may be the same or different, e.g. a solid, or one may be a solid and the other may be a solution. More particularly, where the aromatic composition of the invention is made as a single preparation, there may be prepared, according to ordinary procedures, various types of aromatics such as spray-type aromatics, stand-type aromatics (in the form of a liquid or jelly), and the dissolution-on-use type aromatics such as powders, granules, tablets or capsules used in aqueous solutions such as of effervescent agents. Where the aromatic composition is divided into two preparations, a combination of a perfume and a cyclodextrin and a pH-adjusting substance are separately prepared according to ordinary techniques as an arbitrary preparation such as a liquid, powder, granule, tablet or capsule. Solvents are added to these preparations on use so that both preparations are mixed in the solvent. Thus, a mixing-on-use type aromatic can be obtained.

In the aromatic composition of the type wherein a perfume is included in a cyclodextrin, the perfume is included in spacial or hollow portions of a cylic structure of the cyclodextrin whose inclusion ability is changed depending on the pH in a solution containing these ingredients. The pH of the solution is properly controlled by addition of a pH-adjusting substance so that the release of aroma from the included perfume can be appropriately controlled.

On the other hand, with an aromatic composition comprising a perfume coated with a coating material and a pH-adjusting substance, it is also possible to mix all the ingredients thereby obtaining a single preparation in the form of a solid or solution. Alternatively, the perfume coated with a coating material and a pH-adjusting substance may be separately formed as a solid preparation, or the former may be prepared as a solid preparation and the latter may be prepared as a liquid preparation, thus being as two preparation. More particularly, when the aromatic composition of the invention is formed as a single preparation, there can be prepared a dissolution-on-use type aromatic by preparing an arbitrary solid such as a pill, tablet (including an effervescent tablet) or capsule, according to ordinary techniques. Where the ingredients are separated into two preparations, a perfume coated with a coating material is formed as an arbitrary solid such as a pill, tablet or capsule, and a pH-adjusting substance is prepared as a liquid. A solvent is added on use, if necessary, by which both ingredients are mixed in the solvent to provide a mixing-on-use type aromatic.

In the aromatic composition of the type wherein a perfume is coated with a coating material, the perfume is coated with a coating material whose solubility depends on the pH of a solution containing these ingredients. The pH of the solution is properly controlled by addition of a pH-adjusting substance so that the release of aroma from the coated perfume can be appropriately controlled.

The aromatic composition of the invention is usually used in water, lower alcohols such as methanol, ethanol, propanol and the like, and mixtures thereof.

If a plurality of perfumes are used in the aromatic composition of the invention, different aromas or fragrances may be enjoyed as time passes. More particularly, there are used two types of perfumes in combination, one being an ordinary quick-acting perfume from which an aroma is quickly released from the perfume included in cyclodextrins or coated with coating materials, the other being a release-controlled perfume. In addition, the pH of the solution is varied as time passes.

Moreover, if perfumes which influence the physiological mechanism are contained in the aromatic composition and the release of these perfumes is controlled as set out above thereby causing aromas having mutually contradictory or synergistic actions to be released in relation to the time, such a composition can be applied to the medical treatment of psychosomatic disorder and aromatherapy. For instance, such aromatic compositions may be those which comprise a combination of an antihypnotic perfume and a narcotic perfume or a combination of an appetizing perfume and an anorexigenic perfume. These aromatic composition can control the physiological mechanism by mean of aromas.

Thus, according to the invention, the release control of the perfume can be made by changing the pH of a solution containing such a perfume without resorting to any mechanical means, coupled with advantages that the aromatic composition is inexpensive and has wide utility in various fields since it may be employed in any place. In addition, when the pH-adjusting substance is gradually added or when a plurality of perfumes which have different aroma releasing-rates at a given pH level are used, minute control of the aroma may be possible or different types of aromas may be enjoyed as time passes. Accordingly, the aromatic composition and the aroma control method according to the invention are considered to contribute greatly to aromatherapy and improvements of living environments.

The present invention is more particularly described by way of examples, which should not be construed as limiting the invention thereto. Comparative examples are also described.

EXAMPLE 1

Nine buffer solutions having different pH values in the pH range of from 4 to 7 were provided. $2.5 \times 10^{-3}$ moles of benzyl acetate and $2.5 \times 10^{-3}$ moles of carboxymethylethyl-$\beta$-cyclodextrin (CME-$\beta$-CyD) were dissolved in each buffer solution. The release of the benzyl acetate from these solutions with different pH values was evaluated according to a split-trap method using a release test device shown in FIG. 1. The evaluation of the release was performed under conditions of 25° C. In the release test device of FIG. 1, air flow from an air pump 1 controlled at a rate of 20 cm$^3$/minute by means a flow meter 2. The air is passed through an air inlet pipe 3 into 25 ml of a sample solution 5 contained in a test container 4 (liquid surface area of 63.6 cm$^2$). The benzyl acetate released from the sample solution is passed through an air outlet pipe 6 into an extraction container 7 wherein acetone is placed as an extract solution, followed by release in a gas phase. The benzyl acetate released in the gas phase is quantitatively determined by gas chromatography (GC) under the following conditions. The results of the quantitative determination are shown in FIG. 2.

GC Analysis Conditions
Column: HiCap CBP1-S25-050 (made by Shimadzu Ltd.)
Detector: hydrogen flame ionization detector (made by Shimadzu Ltd.)
Heating rate: 4° C./minute
column temp.: 70° to 220° C.
Flow rate: $N_2$, 2 kg/cm$^2$
Direct Injection From the results of FIG. 2, it will be seen that the release rate of the benzyl acetate increases with an increase in pH of the solution. This is considered for the reason that the CME-$\beta$-CyD has the carboxymethyl group, so that the ratio between the molecular type of CME-$\beta$-CyD and the ion type of CME-$\beta$-CyD, which have different interactions with benzyl acetate, is changed depending on the pH. From the test results, it will become apparent that when the pH of the perfume composition containing CME-$\beta$-CyD is appropriately changed, the release of the aromatic ingredient can be suitably controlled. More particularly, a pH-adjusting substance is added to the perfume composition containing a perfume and CME-$\beta$-CyD to change its pH, by which there can be obtained an aromatic composition capable of release control of the perfume.

COMPARATIVE EXAMPLE 1

Figure 3:
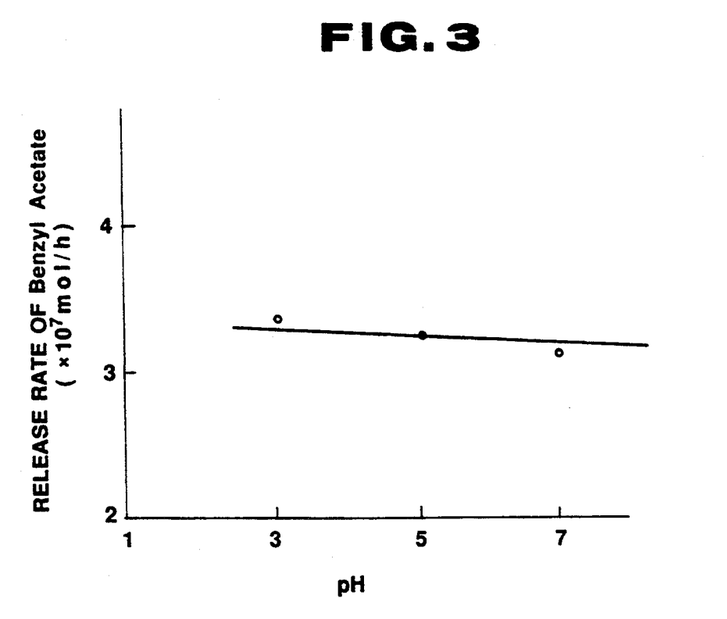
FIG. 3 is a graph showing a release rate of benzyl acetate included in dimethyl-$\beta$-cyclodextrin for comparison in relation to the variation in pH.

$2.5 \times 10^{-3}$ moles of benzyl acetate and $2.5 \times 10^{-3}$ moles of dimethyl-$\beta$-cyclodextrin were dissolved in each of three buffer solutions having pH values of 3, 5 and 7, followed by evaluation of the release of the benzyl acetate in the same manner as in Example 1. The results are shown in FIG. 3, revealing that the release rate of the benzyl acetate did not depend on the pH.

EXAMPLE 2

| [Effervescent tablet composition] | |
|---|---|
| Heavy sodium carbonate | 48 parts |
| Citric acid | 40 |
| Sodium sulfate | 5 |
| Polyethylene glycol 6000 | 1 |
| d-Limonene | 6 |
| Lactose | 5 |
| Total | 105 parts |
| [Enteric coating liquid composition] | |
| Eudragit ® S100 (Röhm Pharma GmbH) | 100 parts |
| Polyethylene glycol 6000 | 10 |
| Talc | 30 |
| Ethanol | 1500 |
| Total | 1640 parts |
| [pH-adjusting tablet composition] | |
| Borax | 20 parts |
| Methyl cellulose | 10 |
| Total | 30 parts |

Figure 4:
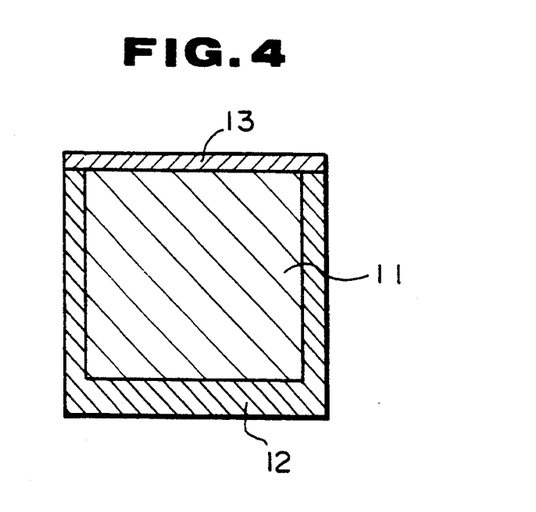
FIG. 4 is a schematic section view of a prolonged release-effervescent tablet.

According to the above formulation of the effervescent tablet, 6 parts of d-limonene was adsorbed on 48 parts of heavy sodium carbonate, followed by addition and mixing of 40 parts of citric acid, 5 parts of sodium sulfate, 1 part of polyethylene glycol 6000 and 5 parts of anhydrous lactose. The mixture was tablated by a tablating machine at a tablating pressure of 2.5 tons/cm$^2$ to obtain tablets with a diameter of 10 mm and a weight of 500 mg/tablet. The resultant tablet was left as it is on one side thereof and coated on the opposite side with a silicone rubber. The left side was coated with eudragit by the means of the enteric coating solution having the above formulation, thereby obtaining a prolonged release-effervescent tablet as shown in FIG. 4. In the figure, reference numeral 11 indicates the tablet, reference numeral 12 indicates the silicone rubber layer, and reference numeral 13 indicates the eudragid layer.

Further, according to the above formulation, 20 parts of borax and 10 parts of methyl cellulose were mixed and tableted to obtain a pH-adjusting tablet having a diameter of 10 mm and a weight of 300 mg/table.

Figure 1:
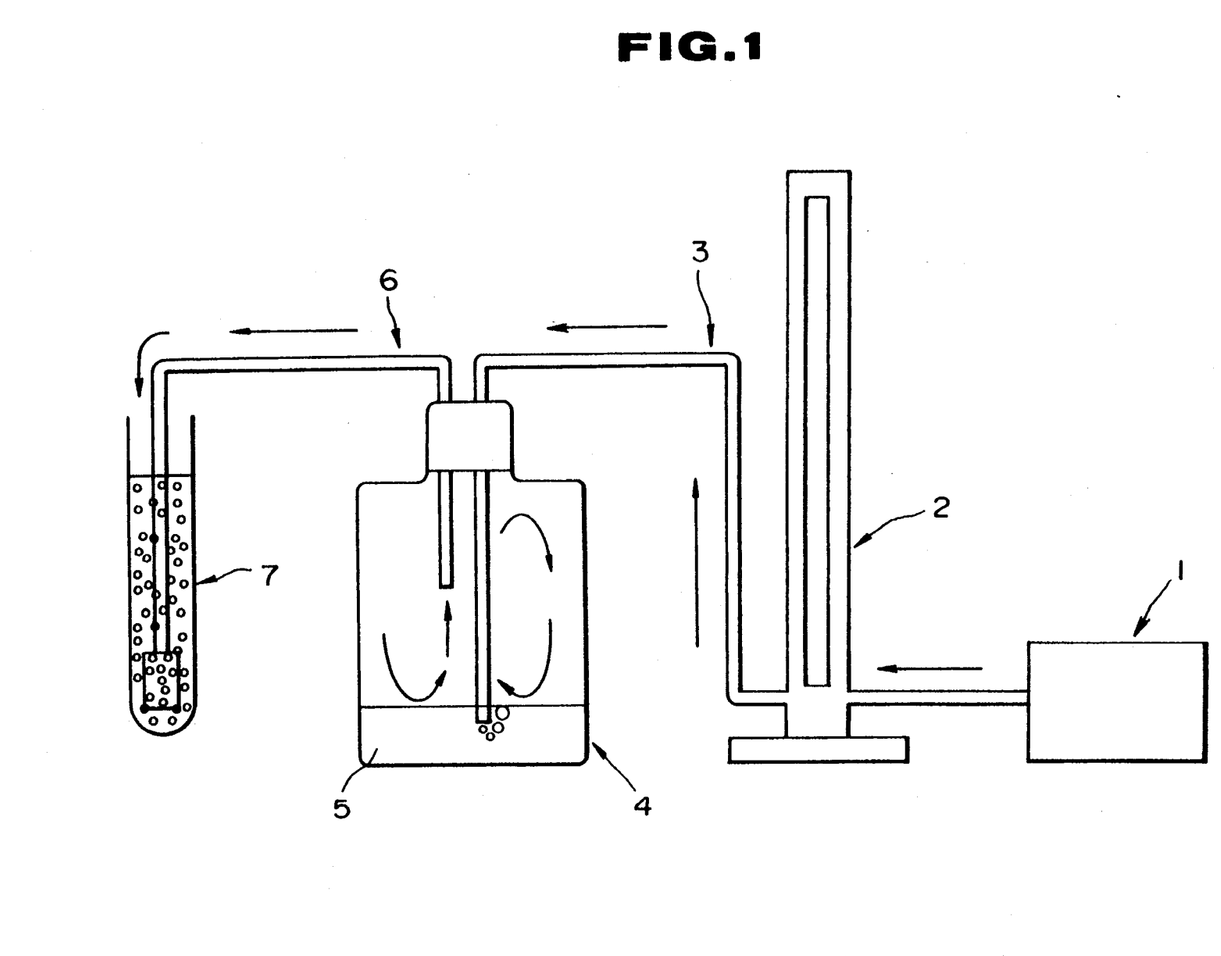
FIG. 1 is an illustrative view of a perfume release testing apparatus.
Figure 2:
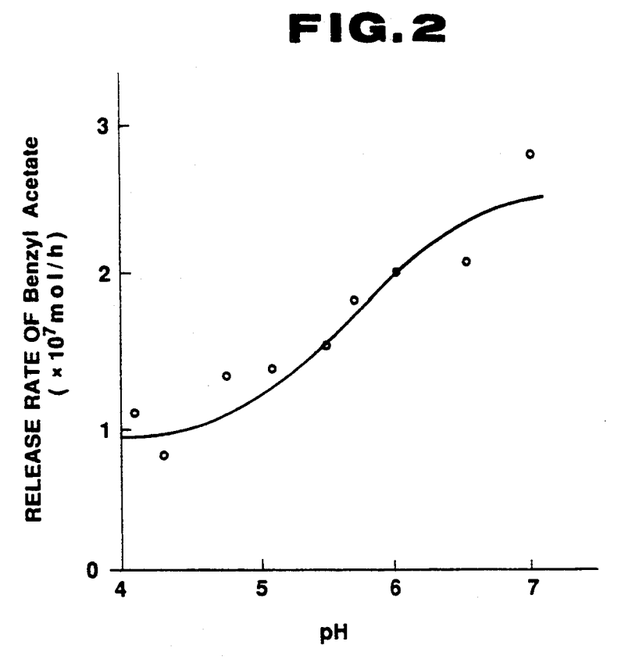
FIG. 2 is a graph showing a release rate of benzyl acetate included in CME-$\beta$-Cyd of Example 1 in relation to the variation in pH.

Subsequently, the thus obtained prolonged release-effervescent tablet and the pH-adjusting tablet were subjected evaluation according to the strip-trap method using a release test device as shown in FIG. 1. The release evaluation was made under conditions of 25° C.

Figure 5:
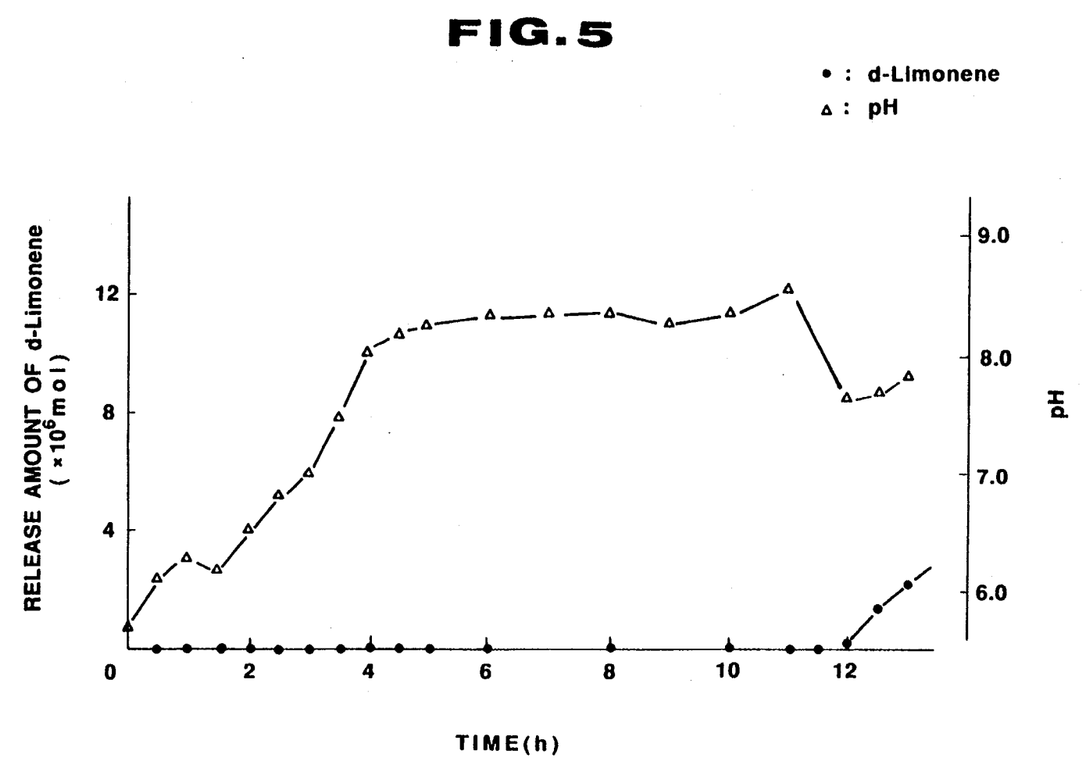
FIG. 5 is a graph showing a release behavior of d-limonene from a prolonged release-effervescent tablet of Example 2 in relation to the variation in pH.

The results of the evaluation reveal that as shown in FIG. 5, a delayed release pattern of d-limonene is obtained from the prolonged release-effervescent tablet. The d-limonene released in the gas phase was quantitatively determined by gas chromatography (GC) under the following conditions.

| GC analysis conditions | |
|---|---|
| Column: | HiCap CBP1-S25-050 (made by Shimadzu Ltd.) |
| Detector: | hydrogen flame ionization detector (made by Shimadzu Ltd.) |
| Heating rate: | 4° C./minute |
| Column temp.: | 70 to 220° C. |
| Flow rate: | $N_2$, 2 kg/ cm$^2$ |
| Direct Injection | |
| Example 3 | |
| [Effervescent tablet A composition] | |
| Heavy sodium carbonate | 48 parts |
| Citric acid | 40 |
| Sodium sulfate | 5 |
| Propylene glycol | 1 |
| d-limonene | 6 |
| Anhydrous lactose | 15 |
| Total | 115 parts |
| [Effervescent tablet B composition] | |
| Heavy sodium carbonate | 48 parts |
| Citric acid | 40 |
| Sodium sulfate | 5 |
| Propylene glycol | 1 |
| Benzyl acetate | 6 |
| Anhydrous lactose | 15 |
| Total | 115 parts |
| [pH-adjusting tablet formulation] | |
| Borax | 10 parts |
| Methyl cellulose | 10 |
| Total | 20 parts |

According to the formulation of the above-effervescent tablet A, 6 parts of d-limonene was adsorbed on 48 parts of heavy sodium carbonate, followed by addition and mixing of 40 parts of citric acid, 5 parts of sodium sulfate, 1 part of propylene glycol and 15 parts of anhydrous lactose. The mixture was tableted by means of a tableting machine at a pressure of 2.5 tons/cm$^2$ to obtain tablets with a diameter of 10 mm and a weight of 500 mg/tablet. Moreover, the tablet was coated with an enteric coating solution and a silicone rubber in the same manner as in Example 2 to obtain a prolonged release-effervescent tablet A.

According to the formulation of the effervescent tablet B, the mixture was tableted in the same manner as for the effervescent tablet A, thereby obtaining effervescent tablet B with a weight of 500 mg/tablet. The effervescent tablet was not subjected to an enteric coating.

Moreover, according to the above formulation, 10 parts of borax and 10 parts of methyl cellulose were mixed and tableted to obtain a pH-adjusting tablet with a diameter of 10 mm and a weight of 300 mg/tablet.

Figure 6:
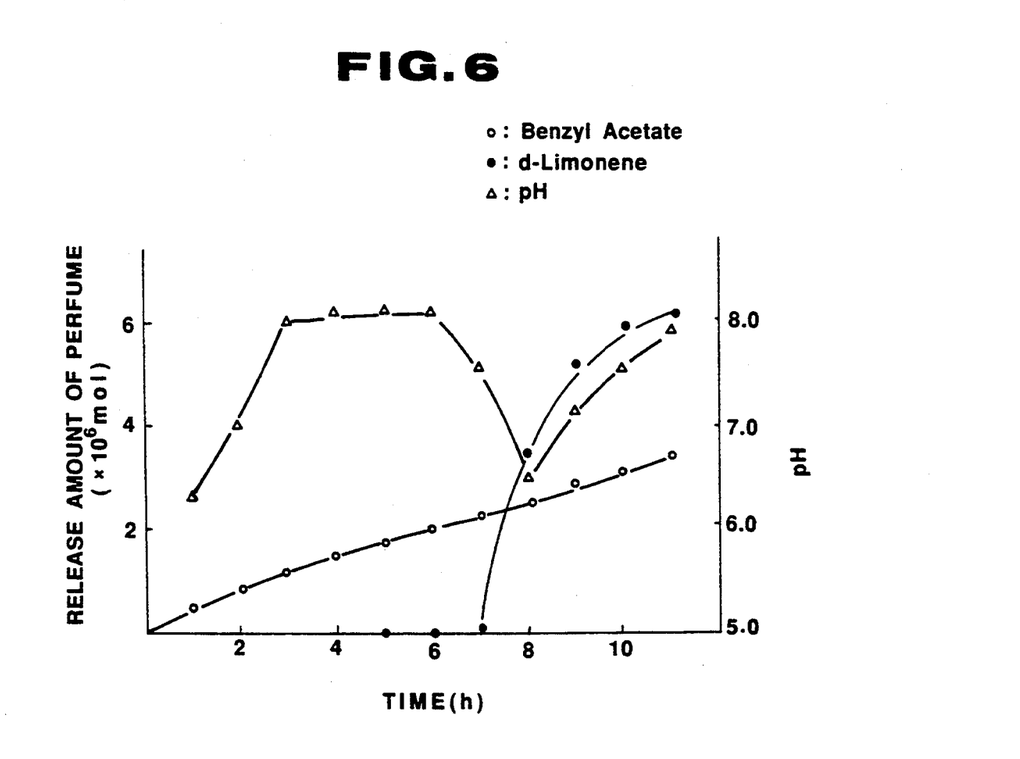
FIG. 6 is a graph showing release a behavior of d-limonene from prolonged release-effervescent tablet A and a behavior of benzyl acetate from effervescent tablet B in relation to the variation in pH.

The thus obtained prolonged release-effervescent tablets A and B and pH-adjusting tablet were set in a release testing device and evaluated. As a result, there were obtained a quick release pattern of benzyl acetate and a delayed release pattern of d-limonene as shown in FIG. 6.

EXAMPLE 4

In the same manner as in Example 2, an effervescent tablet was obtained, followed by spray coating with an enteric coating solution as used in Example 2 by the use of a Hi-coater (Flowint Co., Ltd.), thereby obtaining an enterically coated tablet with a weight of 582 g/tablet.

The results of the above examples and the comparative example reveal that the release of an aroma component from the aroma-containing effervescent tablet of the invention can be delayed or prolonged. Moreover, it will be seen that depending on the type and amount of coating high molecular weight compound, the formulation and compositional ratio of the pH-adjusting tablet, the delaying time and release rate can be arbitrarily controlled.

What is claimed is:

1. An aromatic composition, comprising at least one perfume coated with a material whose solubility in a solvent is dependent on the pH of a solution containing the at least one coated perfume, and a pH-adjusting substance, wherein said material is selected from the group consisting of enteric coating materials which are soluble in alkaline conditions and gastric coating materials which are soluble in acidic conditions, and wherein said composition comprises either a solid preparation whereby said at least one coated perfume and said pH-adjusting substance are dissolved when used, or said composition comprises a solid preparation and a separate liquid preparation whereby said at least one coated perfume and said pH-adjusting substance are mixed when used.

2. The aromatic composition according to claim 1, wherein said enteric coating material is selected from the group consisting of aminoalkylmethacrylate copolymers, methacrylic acid copolymers, hydroxypropylmethyl cellulose phthalate, hydroxypropylmethyl cellulose acetate succinate, carboxymethylethyl cellulose, and cellulose acetate phthalate.

3. The aromatic composition according to claim 1, wherein said composition comprises from 0.01 to 50 wt % of said at least one perfume, based on the total composition.

4. A method for controlling release of at least one perfume, comprising the steps of providing at least one perfume coated with a material whose solubility in a predetermined solvent is dependent on the pH of a solution containing the coated perfume, and changing the pH of the solution containing the at least one coated perfume by addition of a pH-adjusting substance to control the release rate of an aroma from the perfume.

5. The aromatic composition according to claim 1, wherein said material is an enteric coating material.

6. The aromatic composition according to claim 1, wherein said material is a gastric coating material.

7. The aromatic composition according to claim 6, wherein said gastric coating material is polyvinylacetal diethylaminoacetate.

8. The aromatic composition according to claim 3, wherein said composition comprises 0.1 to 30 wt % of said at least one perfume based on the total composition.

9. The aromatic composition according to claim 1, wherein said composition comprises from 0.5 to 30 wt % of said material based on the total composition.

10. The aromatic composition according to claim 9, wherein said composition comprises from 3 to 15 wt % of said material based upon the total composition.

11. The aromatic composition according to claim 1, wherein said composition comprises from 50 to 1,000 parts by weight of said pH-adjusting substance per 100 parts by weight of said material.

12. The aromatic composition according to claim 11, wherein said composition comprises from 100 to 500 parts by weight of the said pH-adjusting substance per 100 parts by weight of said material.

13. The aromatic composition according to claim 1, wherein said pH-adjusting substance is selected from the group consisting of hydrochloric acid, sulfuric acid, boric acid, silicic acid, formic acid, citric acid, trichloroacetic acid, trifluoroacetic acid, benzoic acid, fumaric acid, tartaric acid, methanesulfonic acid, benzenesulfonic acid, p-toluenesulfonic acid, mesitylenesulfonic acid, napththalenesulfonic acid, sodium chloride, sodium hydrogencarbonate, sodium carbonate, borax, sodium sulfate, potassium sulfide, sodium sulfide, sodium sesquicarbonate, potassium oxide, potassium nitrate, sodium nitrate, sodium polyphosphate, calcium carbonate, calcium hydrogenphosphate, potassium bromide, calcium chloride, ammonium chloride, iron sulfate, magnesium carbonate, sodium phosphate, sodium thiosulfate, trimethylamine, triethylamine, tributylamine, pyridine, N,N-dimethylaniline, N-methylpiperidine, N-methylmorpholine, diethylamine, cyclohexylamine, procaine, di-benzylamine, N-benzyl-$\beta$-phenetylamine, 1-ephenamine, and N,N'-dibenzylethylenediamine.

14. The aromatic composition according to claim 1, wherein said perfume is selected from the group consisting of musk oil, civet, castreum, ambergris, sandalwood oil, neroli oil, bergamot oil, lemon oil, lavender oil, sage oil, rosemary oil, peppermint oil, eucalyptus oil, verbena oil, citronella oil, cajuout oil, salvia oil, clove oil, chamomille oil, sandalwood oil, costus oil, labdanum oil, broom extract, carrot seed extract, jasmine extract, mimosa extract, narcissus extract, olibanum extract, rose extract, acetophenone, dimethylindane derivatives, naphthalene derivatives, allyl caprate, $\alpha$-amylcinnamic aldehyde, anethole, anisaldehyde, benzyl acetate, benzyl alcohol, benzyl propionate, borneol, cinnamyl acetate, cinnamyl alcohol, citral citronellal, cumin aldehyde, cyclamen aldehyde, decanol, ethyl butyrate, ethyl caprate, ethyl cinnamate, ethyl vanillin, eugenol, geraniol, hexenol, $\alpha$-hexylcinnamic aldehyde, hydroxycitrolnellal, indole, iso-amyl acetate, iso-amyl iso-valerate, iso-eugenol, linalol, linalyl acetate, p-methylacetophenone, methyl anthranilate, methyl dihydrojasmonate, methyl eugenol, methyl-$\beta$-naphthol ketone, methylphenylcarbinyl acetate, musk ketol, musk xylol, 2,6-nanodinol, $\gamma$-nanolactone, phenyl-acetoaldehydodimethyl acetate, $\beta$-phenylethyl alcohol, 3,3,5-trimethylcyclohexanol, $\gamma$-undecalactone, undecenal and vanillin.

15. The method according to claim 4, wherein the addition of the pH-adjusting substance adjusts the pH of the solution to a value within the range of 3 to 9.

16. The method according to claim 15, wherein the addition of the pH-adjusting substance adjusts the pH of the solution to a value within the range of 4 to 8.

17. The method according to claim 1, wherein said composition comprises a solid composition containing said at least one coated perfume and said pH-adjusting substance.

* * * * *